United States Patent [19]

Heilman et al.

[11] 4,210,149
[45] Jul. 1, 1980

[54] IMPLANTABLE CARDIOVERTER WITH PATIENT COMMUNICATION

[75] Inventors: Marlin S. Heilman, Gibsonia; Alois A. Langer, Pittsburgh, both of Pa.

[73] Assignee: Mieczyslaw Mirowski, Owings Mills, Md.

[21] Appl. No.: 896,518

[22] Filed: Apr. 17, 1978

[51] Int. Cl.² ............................................. A61N 1/36
[52] U.S. Cl. ................................................. 128/419 D
[58] Field of Search ........ 128/419 D, 419 P, 419 PG, 128/419 PS, 419 PT, 419 R

[56] References Cited

U.S. PATENT DOCUMENTS

| | | | |
|---|---|---|---|
| 3,783,877 | 1/1974 | Bowers | 128/419 PS |
| 3,805,795 | 4/1974 | Denniston et al. | 128/419 D |
| 3,952,750 | 4/1976 | Mirowski et al. | 128/419 D |
| 4,041,954 | 8/1977 | O'Hara | 128/419 PT |
| 4,102,346 | 7/1978 | Fulker | 128/419 PT |

*Primary Examiner*—William E. Kamm
*Attorney, Agent, or Firm*—Fleit & Jacobson

[57] ABSTRACT

Disclosed in an implantable cardioverter having the capability of communicating with its wearer. In one specific embodiment, the cardioverter is an automatic, fully implantable ventricular defibrillator including an electrical stimulator to deliver a mild shock to the wearer to inform the wearer, for example, that fibrillation has been sensed. In another embodiment, communication from the implanted defibrillator to the wearer is by means of an implanted audio transducer. And in a third embodiment the implanted defibrillator communicates with the wearer by issuing a mechanical vibration. Also disclosed is a mechanism whereby the wearer is able to disenable the defibrillator, and prevent the delivery of a defibrillating pulse.

19 Claims, 5 Drawing Figures

4,210,149

IMPLANTABLE CARDIOVERTER WITH PATIENT COMMUNICATION

BACKGROUND OF THE INVENTION

Great strides are presently being made to develop an automatic, fully implantable ventricular defibrillator. See, for example, U.S. Pat. Nos. Re. 27,652 and Re. 27,757, where the first concept of the automatic implantable ventricular defibrillator is described. Recent advances have also been made in enhancing the reliability of fibrillation detectors. In this latter regard, see copending U.S. patent applications Ser. Nos. 878,005 and 878,006, each filed on Feb. 15, 1978. Furthermore, as outlined in copending U.S. patent application Ser. No. 801,300, filed on May 27, 1977, steps have been taken to improve the reliability of the implanted defibrillator by the provision of circuitry which interrogates the implanted electronics to verify proper operation before a defibrillating shock is delivered.

Each of the foregoing advances is significant, and yet it must be recalled that the art of implantable defibrillators is in its infancy. Accordingly, there is a need for a patient communication channel in the implantable defibrillator, both for the peace of mind of the wearer (to know that his implanted device can be electively disenabled and explanted) and to avoid discomfort to the wearer (should the sensing circuit actually malfunction). In addition, there are other reasons for wanting wearer-recognizable stimuli to be delivered by the implanted defibrillator to the wearer.

It is toward the provision of an implantable defibrillator having a communication channel, that the present invention is directed.

SUMMARY OF THE INVENTION

The present invention relates to the field of cardioversion, and more particularly to circuitry for use in an implanted cardioverter which provides a communication link between the cardioverter and its wearer. As used herein, "Cardioverting" or "cardioversion" is intended to encompass the correction of a number of arrhythmic heart conditions, both lethal and non-lethal. Those arrhythmic heart conditions include atrial tachycardia, atrial flutter, atrial fibrillation, junctional rhythms, ventricular tachycardia, ventricular flutter, and ventricular fibrillation, and any other non-pacemaking related arrythmic condition which may be corrected by applying electrical shocks to the heart. Obviously then, "defibrillation" is included in the term cardioversion as a method of applying electrical shocks to the heart to defibrillate fibrillating atria or fibrillating ventricles.

Specifically, the present invention relates to the provision of a communication link, in the form of an electrical stimulus, a mechanical vibration or an audible signal, which alerts the patient, for example, that fibrillation has been sensed. In a specific example, an audible signal is sounded at such time when the patient should be unconscious if undergoing ventricular fibrillation; in this way, if the patient is conscious when the audible signal is issued, there has, in all probability, been an erroneous detection of fibrillation, and the patient can take steps to disenable the defibrillator before the delivery of a shock. It is, on the other hand, possible to time the audible signals so that they occur prior to such time when unconsciousness usually results, in this manner serving as an alert to the patient that unconsciousness will follow and that a shock will be delivered. Other information can be indicated by the communication link.

Also a part of the present invention is an external control device which can be used by the patient to disenable the implanted defibrillator. In this manner, should the patient receive a signal indicating that fibrillation was sensed when indeed there was no fibrillation, the patient could disenable his implanted device, see his physician, and schedule the explanation of his device. There may, of course, be other reasons for the patient (or his physician) to disenable the implanted device, as, for example, preliminary to surgery.

It is accordingly a principal object of the present invention to provide a communication channel in an implanted defibrillator so that there can be communication between the defibrillator and its wearer.

A more specific object of the present invention is to provide a communication link for implementation in a defibrillator so that the patient may be made aware of the imminence of a defibrillating shock.

Still another specific object of the present invention is to provide an implanted defibrillator with a mechanism for electively disenabling the defibrillator and preventing the delivery of a shock.

These and other objects of the present invention, as well as many of the attendant advantages thereof, will become more readily apparent when reference is made to the following description, taken in conjunction with the accompanying drawings.

DETAILED DESCRIPTION OF THE DRAWINGS

Figure 1:
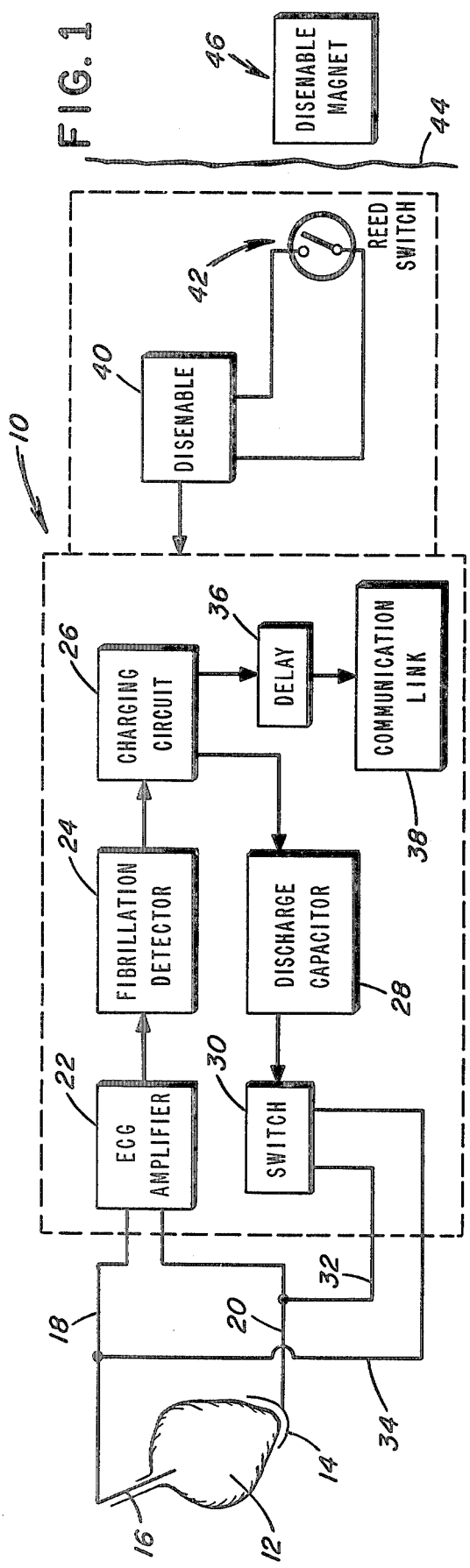
FIG. 1 is a block diagram of a defibrillator designed in accordance with the teachings of the present invention.

With reference first to FIG. 1, the overall concept of the implantable defibrillator and the inventive communication channel will be described. In FIG. 1 an implanted defibrillator is shown generally at 10. Defibrillator 10 associates with a heart 12 through the means of a conformal apex electrode 14 and a superior vena cava catherer electrode 16. A pair of leads 18 and 20 bring ECG impulses from electrodes 14 and 16 to an ECG amplifier 22. During a fibrillation detection mode, fibrillation is detected by a fibrillation detector 24 which can be of a design such as any of those described in the patents and patent applications noted above. Then, once fibrillation is detected the defibrillator goes into a defibrillation shock delivering mode, during which, a charging circuit 26 is actuated, and, when a discharge capacitor 28 is sufficiently charged, energy from the capacitor is released by a switch 30 so that a defibrillating shock is delivered to the heart 12 through electrodes 14 and 16 via leads 32 and 34, respectively.

Thus far, the defibrillator is conventional and is fully described in several of the references noted above. As further shown in FIG. 1, however, the defibrillator 10 includes a delay element 36 and a communication link 38. In this manner, a signal will be issued at a predetermined time after charging circuit 26 is actuated. Also schematically illustrated in FIG. 1, is a disenable circuit 40 associated with a reed switch 42. The skin of the wearer is indicated at 44, and a disenable magnet is shown at 46.

In operation, assuming that delay element 36 is set for a time longer than it takes for ventricular fibrillation to result in unconsciousness, but shorter than the time it takes to deliver a defibrillating shock to the heart, a conscious wearer will be made aware of an erroneous fibrillation diagnosis, and can take appropriate action to disenable his implanted device before the delivery of a defibrillating shock. This is accomplished by the patient bringing his disenable magnet 46 in proximity to the implanted reed switch 42. Reed switch 42 would then cause circuit 40 to issue a disenabling command to one or more of switch 30, charging circuit 26, or fibrillation detector 24. Then the patient could contact his physician, and if necessary, could schedule surgery to explant the device.

As noted above, alarm 38 can function other than as an indication to the conscious patient that the detector erroneously diagnosed fibrillation. In this regard, delay element 36 could be set for any given delay so that a signal could be delivered to the conscious patient at any time either during a fibrillation event or otherwise.

Figure 2:
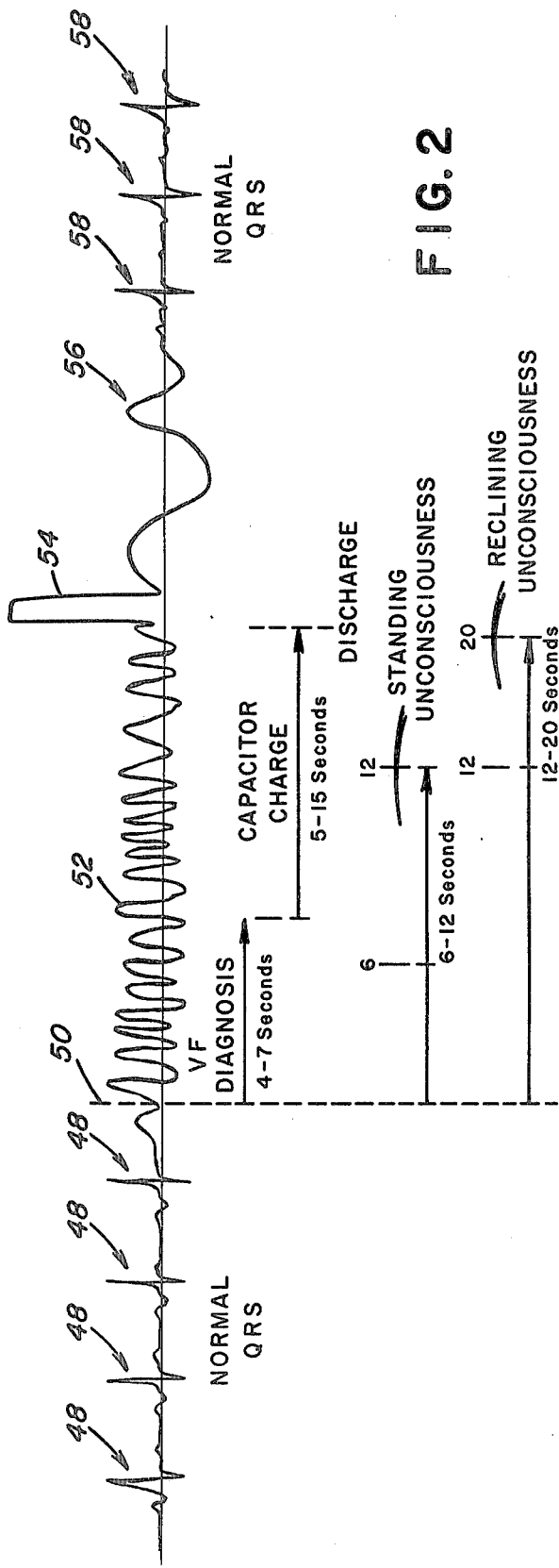
FIG. 2 is an illustration representing typical time sequences involved in ventricular fibrillation and defibrillation.

With reference now to FIG. 2, a typical time sequence of a fibrillation event will be described. In FIG. 2, normal QRS complexes are shown at 48. At a time indicated at 50, fibrillation commences and the fibrillation waveform is indicated at 52. As can be seen, ventricular fibrillation can be diagnosed in somewhere between four and seven seconds, and from the diagnosis, the capacitor can be charged and discharged in an additional five to fifteen seconds. In FIG. 1, a defibrillating pulse is indicated at 54, and the ECG of a recovering heart is shown at 56. Normal QRS complexes following successful defibrillation can be seen at 58. Also indicated in FIG. 2 are typical times when unconsciousness results from ventricular fibrillation. As can be seen, an individual who is standing becomes unconscious in somewhere between six and twelve seconds after the onset of fibrillation. A reclining individual, on the other hand, does not become unconscious until somewhere in the neighborhood of twelve to twenty seconds after fibrillation commences.

From FIG. 2, it should be clear how delay 36 is set to accomplish any of the possible functions of the communication link. The time of capacitor discharge and other parameters could also be varied to permit the communication signal to be issued as desired.

Figure 3:
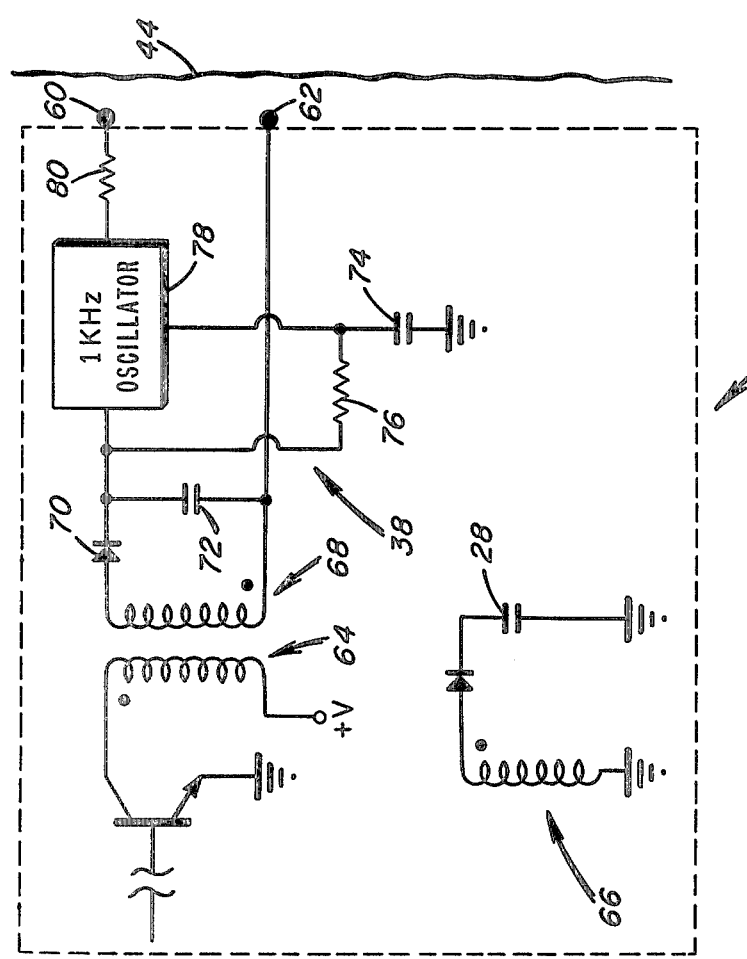
FIG. 3 is a circuit schematic illustrating a communication link which stimulates a wearer through mild electrical shock.

With reference then to FIG. 3, a first specific embodiment of the inventive communication link, where the patient is stimulated by a mild electrical shock, will be described. For purposes of illustration, the external surface of the implanted defibrillator is indicated at 10. On this surface, but insulated therefrom, are a pair of closely-spaced conductive buttons 60 and 62. Buttons 60 and 62 serve to deliver a mild shock to the patient, and are therefore placed in close proximity to the under surface of the skin 44, where nerve endings are in abundance.

The major portion of the defibrillator circuitry has been omitted from FIG. 3 so as to facilitate an explanation of the inventive communication link circuit 38. Discharge capacitor 28 is shown in FIG. 3 as is a portion of the inverter circuit which charges capacitor 28. The inverter circuit includes a transformer having windings 64, 66 and 68. Suffice it to say for purposes of this application, that winding 68 in the circuit of communication link 38 is actuated once fibrillation is detected and discharge capacitor 28 is being charged.

When capacitor 28 is being charged, winding 68 is excited, and through the means of rectifying diode 70 and filter capacitor 72, an integrating capacitor 74 is charged through resistor 76. Once the voltage on capacitor 74 reaches a predetermined level, a voltage controlled oscillator 78 is actuated and issues a signal to buttons 60 and 62 through a current limiting resistor 80. The function of resistor 80 is to maintain the current at approximately 1 ma. In the circuit of FIG. 3, the delay is determined by the values of capacitor 74 and resistor 76, and can be set as desired.

Figure 4:
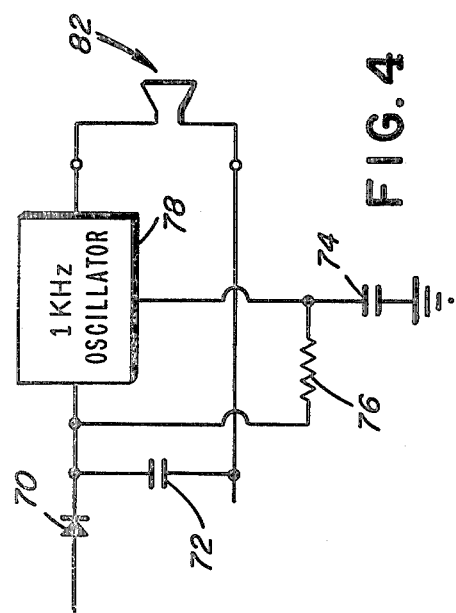
FIG. 4 is a partial circuit schematic of an alternative communication link wherein an acoustical signal is employed rather than electrical shock.

With reference now to FIG. 4, a second embodiment of the inventive communication link will be described. In FIG. 4, rather than a signal which alerts the wearer by electrical stimulation, there is disclosed a communication link including an audio output such as a piezoelectric audio alert transducer 82. Examples of such an audio transducer are Linden Laboratories Inc., State College, Pa., transducer Models Nos. 70065 and 70067. It should be noted that in FIG. 4, current limiting resistor 80 has been eliminated from the circuit between oscillator 78 and the patient stimulator, in this case, audio transducer 82. In all other respects, the circuits of FIGS. 3 and 4 are identical, and hence the circuit of FIG. 4 will not be described in detail.

Figure 5:
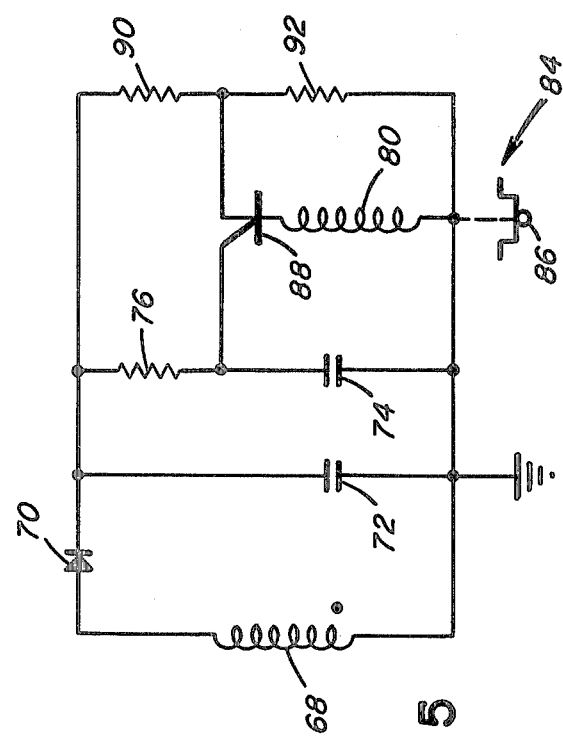
FIG. 5 is a circuit schematic of still a further communication link, wherein mechanical stimulation of the wearer is practiced.

In FIG. 5, there is illustrated still a third embodiment of the invention communication link, this involving mechanical stimulation of the patient. In this embodiment, a mechanical vibrator is shown generally at 84 and has a plunger tip 86 which is acuted by a coil 88 of microsolenoid. Solenoid 80 is energized by a programmable unijunction transistor 88 which is fired when the voltage of capacitor 74 exceeds a reference voltage set by voltage divider resistors 90 and 92.

In operation, winding 68 is energized when discharge capacitor 28 is being charged by the inverter circuit. Capacitor 74 therefore begins to charge through resistor 76, while a reference voltage is impressed on the unijunction transistor by voltage divider resistors 90 and 92. When the voltage across capacitor 74 increases to above the reference voltage, unijunction transistor 88 fires, solenoid 80 is actuated, and the plunger 86 stimulates the patient. Capacitor 74 is thereby discharged and the unijunction transistor again becomes nonconductive. With coil 68 still excited, however, the cycle is repeated. This cycling continues at a relatively low frequency and the patient is therefore made aware of the movement of plunger 86 through his tactile senses.

Above, several embodiments of the present invention have been described. It should be understood, however, that these specific embodiments were described for purposes of illustration only, and are in no way intended to limit the scope of the present invention. Rather, it is the intention that the present invention be limited only as defined in the appended claims.

What is claimed is:

1. A patient communication system for use in a cardioverter encased in a housing implanted in a patient, the cardioverter including a detector for detecting the onset of fibrillation, a discharge device operative at the expiration of a first time interval subsequent to the detection of said fibrillation for discharging defibrillating energy in the form of a defibrillating shock through the heart of the patient, and a charging device made active subsequent to the detection of said fibrillation for charging the discharge device with sufficient energy to effect defibrillation, said patient communication system comprising:

implanted communication means for issuing a communication signal capable of detection by the patient, said communication means including a pair of implanted electrodes arranged to deliver a mild shock to the patient, at least one of said electrodes being disposed on an exterior surface of said implanted housing; and implanted triggering means for actuating said communication means in response to a given condition of the implanted cardioverter.

2. The system recited in claim 1, and further comprising: delay means for delaying the issuance of said communication signal for a predetermined time after recognition of said condition.

3. The system recited in claim 2, wherein said delay means delays the issuance of said communication signal for a time longer than twelve seconds.

4. The system recited in claim 2, wherein said delay means delays the issuance of said communication signal for a time longer than twenty seconds.

5. The system recited in claim 1, further comprising means for insulating said at least one electrode from said exterior surface.

6. The system recited in claim 1, wherein each one of said pair of implanted electrodes is a button electrode.

7. In combination, an implantable defibrillator and an implantable patient communication system, said implantable defibrillator comprising detector means for detecting the onset of fibrillation,
   discharge means operative at the expiration of a first time interval subsequent to the detection of said fibrillation for discharging defibrillating energy through the heart of a wearer in need of defibrillation, and
   charging means activated subsequent to the detection of said fibrillation for charging said discharge means with sufficient energy to effect defibrillation, and
   said patient communication system comprising
   implanted signal-generating means, responsive to the activation of said charging means, for producing a communication signal at a time prior to the end of said first time interval but after the activation of said charging means; and
   implanted communication means responsive to said communication signal for producing an alert capable of detection by the patient, said alert indicating that the defibrillating energy is about to be delivered.

8. The system of claim 7, wherein said communication means includes a pair of implanted electrodes arranged to deliver a mild shock to the patient, at least one of said electrodes being disposed on an exterior surface of said implanted housing.

9. The system recited in claim 8, further comprising means for insulating said at least one electrode from said exterior surface.

10. The system recited in claim 8, wherein each one of said pair of implanted electrodes is a button electrode.

11. A patient communication system for use in a cardioverter encased in a housing implanted in a patient, the cardioverter including a detector for detecting the onset of fibrillation, a discharge device operative at the expiration of a first time interval subsequent to the detection of said fibrillation for discharging defibrillating energy in the form of a defibrillating shock through the heart of the patient, and a charging device made active subsequent to the detection of said fibrillation for charging the discharge device with sufficient energy to effect defibrillation, said patient communication system comprising:

implanted signal-generating means, responsive to the activation of said charging device, for producing a communication signal at a time prior to the end of said first time interval but after the activation of said charging device; and
   implanted communication means responsive to said communication signal for producing an alert capable of detection by the patient, said alert indicating that the defibrillating shock is about to be delivered.

12. The system recited in claim 11, wherein said alert is electrical stimulation.

13. The system recited in claim 11, wherein said alert is acoustical stimulation.

14. The system recited in claim 11, wherein said alert is mechanical stimulation.

15. The system recited in claim 11, and further comprising: disenable means for preventing the discharge of energy from said discharge means; and external command means for actuating said disenable means.

16. The system of claim 11, wherein said communication means includes a pair of implanted electrodes arranged to deliver a mild shock to the patient, at least one of said electrodes being disposed on an exterior surface of said implanted housing.

17. The system recited in claim 16 further comprising means for insulating said at least one electrode from said exterior surface.

18. The system recited in claim 16, wherein each one of said pair of implanted electrodes is a button electrode.

19. A patient communication system for use in a cardioverter encased in a housing implanted in a patient, the cardioverter being operative, first, in a fibrillation detecting mode and, then, in a defibrillation shock delivering mode, the cardioverter including a detector for detecting the onset of fibrillation, a discharge device operative at the expiration of a first time interval subsequent to the detection of said fibrillation for discharging defibrillating energy in the form of a defibrillating shock through the heart of the patient, and a charging device made active subsequent to the detection of said fibrillation for charging the discharge device with sufficient energy to effect defibrillation, said patient communication system comprising:

implanted signal-generating means, responsive to the detection of said fibrillation, for producing a communication signal at a time prior to the end of said first time interval but after the activation of said charging device, wherein said communication signal indicates that the cardioverter has entered said defibrillation shock delivering mode; and
   implanted communication means responsive to said communication signal for producing an alert capable of detection by the patient, said alert indicating that the defibrillating shock is about to be delivered.

* * * * *